US008323342B2

(12) United States Patent
Schwab

(10) Patent No.: US 8,323,342 B2
(45) Date of Patent: Dec. 4, 2012

(54) INTERVERTEBRAL IMPLANT

(76) Inventor: Frank J. Schwab, New York, NY (US)

(*) Notice: Subject to any disclaimer, the term of this patent is extended or adjusted under 35 U.S.C. 154(b) by 1049 days.

(21) Appl. No.: 11/436,006

(22) Filed: May 17, 2006

(65) Prior Publication Data

US 2006/0265068 A1 Nov. 23, 2006

Related U.S. Application Data

(60) Provisional application No. 60/700,197, filed on Jul. 18, 2005, provisional application No. 60/681,793, filed on May 17, 2005.

(51) Int. Cl.
*A61F 2/44* (2006.01)
(52) U.S. Cl. .............. 623/17.14; 623/17.11; 623/17.15; 623/17.16
(58) Field of Classification Search ..... 623/17.11–17.16
See application file for complete search history.

(56) References Cited

U.S. PATENT DOCUMENTS

| | | | | |
|---|---|---|---|---|
| 5,425,773 A * | 6/1995 | Boyd et al. | ............... | 623/17.15 |
| 5,893,889 A * | 4/1999 | Harrington | ............... | 623/17.16 |
| 6,019,792 A * | 2/2000 | Cauthen | ............... | 623/17.14 |
| 6,063,121 A * | 5/2000 | Xavier et al. | ............... | 623/17.15 |
| 6,488,710 B2 * | 12/2002 | Besselink | ............... | 623/17.15 |
| 6,811,567 B2 | 11/2004 | Reiley | | |
| 7,201,776 B2 * | 4/2007 | Ferree et al. | ............... | 623/17.16 |
| 7,465,317 B2 * | 12/2008 | Malberg et al. | ............... | 623/17.11 |
| 2003/0074076 A1 * | 4/2003 | Ferree et al. | ............... | 623/17.16 |
| 2004/0024460 A1 * | 2/2004 | Ferree | ............... | 623/17.12 |
| 2004/0039448 A1 * | 2/2004 | Pisharodi | ............... | 623/17.15 |
| 2004/0044410 A1 * | 3/2004 | Ferree et al. | ............... | 623/17.13 |
| 2005/0043800 A1 * | 2/2005 | Paul et al. | ............... | 623/17.15 |
| 2005/0131542 A1 * | 6/2005 | Benzel et al. | ............... | 623/17.13 |
| 2005/0154468 A1 * | 7/2005 | Rivin | ............... | 623/17.16 |

* cited by examiner

*Primary Examiner* — Alvin Stewart
*Assistant Examiner* — Julianna N Harvey
(74) *Attorney, Agent, or Firm* — Senniger Powers LLP

(57) ABSTRACT

An intervertebral implant for separating an upper vertebra and a lower vertebra. The implant includes an upper mount having a first surface sized and shaped for mounting on the upper vertebra and a second surface opposite the first surface. The implant includes a lower mount having a first surface sized and shaped for mounting on the lower vertebra and a second surface opposite the first surface. The implant includes an element positioned between the upper mount and the lower mount spacing the first surface of the upper mount from the first surface of the lower mount by a predetermined distance. The element is configured to permit the upper mount to pivot relative to the lower mount. The element allows the upper vertebra to pivot relative to the lower vertebra while maintaining spacing between the upper vertebra and the lower vertebra.

8 Claims, 13 Drawing Sheets

INTERVERTEBRAL IMPLANT

CROSS-REFERENCE TO RELATED APPLICATIONS

This application claims priority from U.S. Provisional Patent Application No. 60/681,793 filed May 17, 2005, entitled, "Ensemble of Devices and Methods for Dynamic Posterior Spinal Stabilization", and U.S. Provisional Patent Application No. 60/700,197 filed Jul. 18, 2005, entitled, "Posteriorly Placed Intervertebral Dynamic Implant". Both of these applications are incorporated by reference.

BACKGROUND

The present invention relates to implants and, more particularly, to intervertebral implants.

Vertebrae of the human spine are arranged in a column with one vertebra positioned on top of the next. An intervertebral disc is positioned between each vertebrae pair to provide a cushion between the adjacent vertebrae and transmitting forces. The discs permit movement between vertebra so the column can twist, bend, stretch and compress. Disease, injury, surgery and spinal degeneration can adversely affect the normal function of the intervertebral disc and the complex interrelationship between adjacent vertebrae of the spinal column. Sometimes pain results from diseased, injured or degenerated discs. Because the spinal column is frequently moved, resulting pain can occur frequently to afflicted humans, substantially diminishing quality of life.

Conventionally, surgeons treat malfunctioning discs by surgically removing the disc and immobilizing the adjoining vertebrae so they fuse together over time. Such procedures permanently prevent motion between the affected vertebrae, potentially increasing stress on other healthy spinal segments. The increased stress can accelerate disc degeneration. Over time, the increased stress can cause disc herniation, instability and arthritis in the previously healthy segments. Thus, there is a need for a system and method that treats malfunctioning discs without significantly increasing stress on other discs and adversely affecting them.

BRIEF SUMMARY

The present invention relates to an intervertebral implant for separating an upper vertebra and a lower vertebra. The implant comprises an upper mount having a first surface sized and shaped for mounting on the upper vertebra and a second surface opposite the first surface. The implant also includes a lower mount having a first surface sized and shaped for mounting on the lower vertebra and a second surface opposite the first surface. In addition, the implant has an element positioned between the upper mount and the lower mount spacing the first surface of the upper mount from the first surface of the lower mount by a predetermined distance. The element is configured to permit the upper mount to pivot relative to the lower mount and allows the upper vertebra to pivot relative to the lower vertebra while maintaining spacing between the upper vertebra and the lower vertebra.

In another aspect, the present invention relates to an intervertebral implant for separating an upper vertebra and a lower vertebra. The implant comprises an upper mount having a upper surface sized and shaped for mounting on the upper vertebra and a lower surface opposite the first surface. Further, the implant includes a lower mount having a lower surface sized and shaped for mounting on the lower vertebra and a upper surface opposite the first surface. The implant also comprises an element positioned between the upper mount and the lower mount spacing the upper surface of the upper mount from the lower surface of the lower mount by a predetermined distance. The element is configured to permit the upper mount to pivot relative to the lower mount, thereby allowing the upper vertebra to pivot relative to the lower vertebra while maintaining spacing between the upper vertebra and the lower vertebra.

In yet another aspect, the present invention relates to an intervertebral implant for separating an upper vertebra and a lower vertebra comprising an upper mount having a forward facing surface sized and shaped for mounting on the upper vertebra. The upper mount also has a rearward facing surface opposite the forward facing surface. Further, the implant includes a post extending downward from the upper mount and a lower mount having a forward facing surface sized and shaped for mounting on the upper vertebra. The lower mount also has a rearward facing surface opposite the forward facing surface and a channel sized and shaped for pivotally receiving the post so the upper mount pivots relative to the lower mount. This allows the upper vertebra to pivot relative to the lower vertebra while maintaining spacing between the upper vertebra and the lower vertebra.

The present invention also relates to a method of implanting an intervertebral implant comprising a plurality of components. Each of the plurality of components connects to another component of the plurality of components. The method comprises removing at least a portion of a natural disc from between an upper vertebra and a lower vertebra. A first component of the plurality of components is inserted between the upper vertebra and the lower vertebra, and a second component of the plurality of components is inserted between the upper vertebra and the lower vertebra. The first component of the intervertebral implant is connected to the second component of the intervertebral implant.

While the invention has been described with reference to the preferred embodiment(s) thereof, it will be appreciated by those of ordinary skill in the art that various modifications can be made to the invention itself without departing from the spirit and scope thereof. All changes and modifications that are within the spirit of the invention are desired to be protected.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
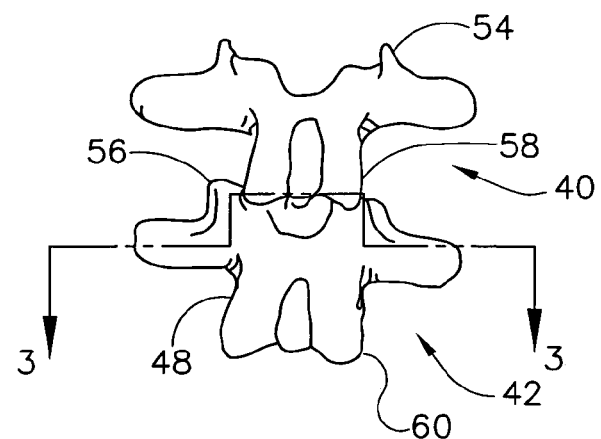
FIG. 1 is a rear elevation of two lumbar vertebrae.
Figure 2:
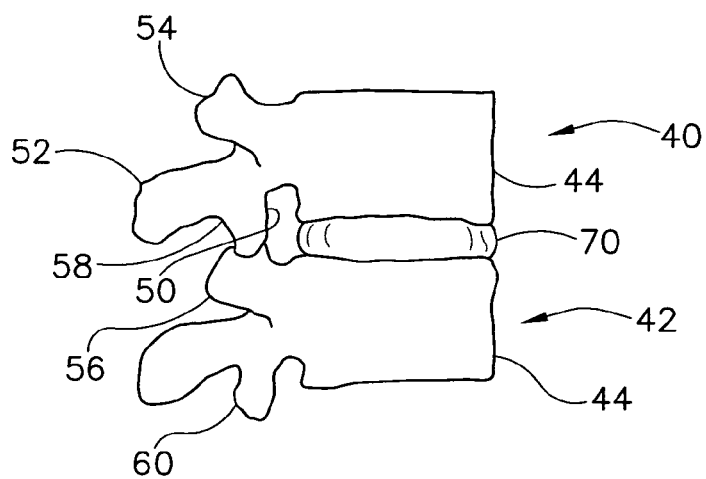
FIG. 2 is a side elevation of two lumbar vertebrae.
Figure 3:
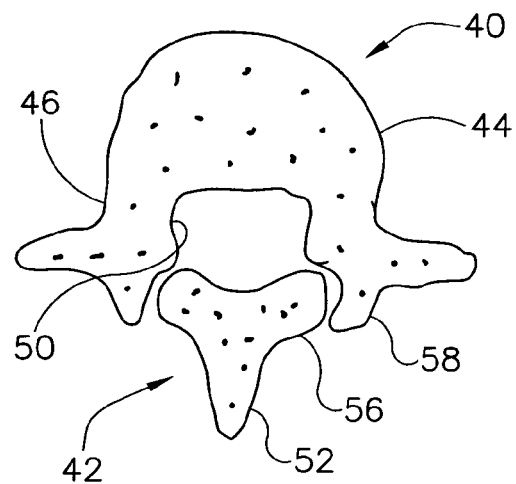
FIG. 3 is a cross section of the vertebrae taken along line 3-3 of FIG. 1.

Referring to the figures, and more particularly to FIGS. 1-3, adjacent upper (or cephalad) and lower (or caudal) vertebrae are designated in their respective entireties by reference numbers 40 and 42. Each of the vertebra 40, 42 includes a body 44. Portions of the vertebrae known as pedicles 46 extend rearward from each body 44 to lamina 48 extending across the rearward ends of the pedicles. The body, pedicles and lamina surround a spinal canal (or vertebral foramen) 50, which receives the spinal cord (not shown). A central rearward protrusion known as a spinous process 52 extends rearward from the lamina 48. Each vertebra 40, 42 also includes upper facets (or superior articular processes) 54, 56 (respectively) extending obliquely outward from the lamina 48 on opposite sides of the spinous processes 52. The vertebrae 40, 42 also include lower facets (or inferior articular processes) 58, 60 (respectively) extending downward adjacent the corresponding spinous processes 52. Portions of the upper facets 56 of the lower vertebrae 42 overlap the lower facets 58 of the upper vertebrae 40 as shown in FIG. 3, to form facet joints allowing the spine to bend forward and backward (i.e., to articulate), and twist. As shown in FIG. 2, an intervertebral disc 70 is positioned between the upper and lower vertebrae 40, 42. The disc 70 separates and provides cushion between the vertebrae 40, 42. A strong ligament (not shown) extends between the vertebrae 40, 42 along the rearward wall of the spinal canal 50 to prevent the vertebrae from separating.

Figure 4:
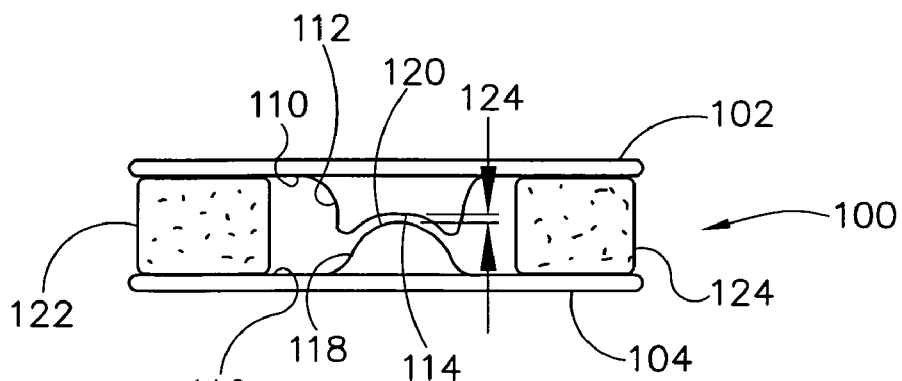
FIG. 4 is a is a side elevation of an intervertebral implant of a first embodiment of the present invention.

Referring to FIG. 4, an intervertebral implant of a first embodiment is designated in its entirety by the reference number 100. The implant 100 includes an upper plate or mount 102 and a lower plate or mount 104. The upper plate 102 includes a lower face 110 and a protrusion 112 having a concave lower end 114 extending downward from the lower face. The lower plate 104 includes an upper face 116 and a protrusion 118 having a convex upper end 120 extending upward from the upper face. The concave end 114 of the upper plate protrusion 112 receives the convex end 120 of the lower plate protrusion 118. The concave end 114 and the convex end 120 have complementary shapes (e.g., similarly sized spherical shapes) allowing the upper and lower plates 102, 104 to pivot with respect to each other. Although the concave end 114 and the convex end 120 may have other radii without departing from the scope of the present invention, in one embodiment the concave end has a radius of between about 3 millimeters (mm) and about 15 mm, and the convex end has a radius of between about 3 mm and about 20 mm. In one particular embodiment, the concave end 114 has a radius of about 4 mm and the convex end 120 has a radius of about 4.5 mm. Although the upper plate protrusion 112 and the lower plate protrusion 118 may have other overall lengths without departing from the scope of the present invention, in one embodiment the protrusions have equal lengths of between about 8 mm and about 20 mm. In one particular embodiment, upper plate protrusion 112 and the lower plate protrusion 118 both have a length of about 12 mm. In an alternate embodiment, it is envisioned the protrusions 112, 118 may have different lengths from each other and/or the convex and concave ends 120, 114 may be switched.

As further illustrated in FIG. 4, the implant 100 includes a forward compressible element or cushion 122 positioned between the upper and lower plates 102, 104 in front of (or anterior to) the protrusions 112, 118 and a rearward compressible element or cushion 124 positioned between the upper and lower plates behind (or posterior to) the protrusions. The compressible elements 122, 124 provide some resistance to movement of the plates 102, 104, but compress to allow the plates to pivot. Thus, the elements 122, 124 stabilize the plates 102, 104. Although the elements 122, 124 may be joined to the plates 102, 104 in other ways without departing from the scope of the present invention, in one embodiment the elements are adhesively bonded to the plates using a non-toxic adhesive having a suitable strength. In other embodiments, it is envisioned that other conventional fasteners and bonding materials may be used in addition to or instead of the adhesive.

Although the plates 102, 104 may be made of other materials without departing from the scope of the present invention, in one embodiment the plates are made from a cobalt alloy or a surgical steel. Although the compressible elements 122, 124 may be made of other materials without departing from the scope of the present invention, in one embodiment the compressible elements are made from polyurethane or other polymer. Although the compressible elements 122, 124 may be have other compressive stiffness modulii without departing from the scope of the present invention, in one embodiment the compressible elements have a compressive stiffness modulus approximately equal to a natural disc. In one embodiment, the compressible elements 122 124 have an undeformed thickness of between about 3 mm and about 15 mm, providing an unloaded vertical gap 124 between the concave end 114 of the upper plate protrusion 112 and the convex end 120 of the lower plate protrusion 118 of between about 0.1 mm and about 3 mm.

To install the implant 100, the damaged disc 70 is removed using conventional surgical techniques. The implant 100 is inserted between the vertebrae 40, 42 once the disc 70 is removed. Depending upon the particular disc being replaced and other factors understood by those skilled in the art, the implant 100 may be inserted between the vertebrae from the rear or from the front. The implant 100 is anchored in place between the vertebrae 40, 42 using conventional techniques, including using adhesives, screws and integral fasteners. Unlike many conventional implants, which encourage the vertebrae 40, 42 to fuse, this implant 100 replaces the disc 60 and provides movement.

Figure 5:
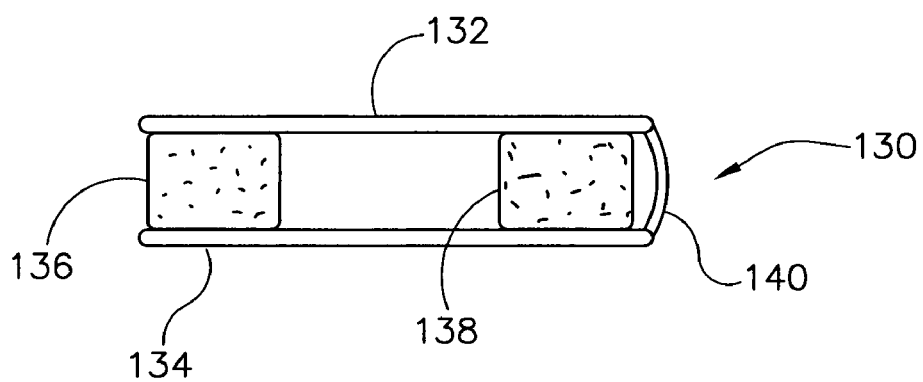
FIG. 5 is a side elevation of an intervertebral implant of a second embodiment of the present invention.

FIG. 5 illustrates an intervertebral implant of a second embodiment, generally designated by 130. This implant 130 includes an upper plate 132 and a lower plate 134. These plates 132, 134 are similar to those of the first embodiment but do not have protrusions. The implant 130 also includes a forward compressible element 136 and a rearward compressible element 138 behind the forward compressible element. Although the compressible elements 136, 138 may be made of other materials without departing from the scope of the present invention, in one embodiment the compressible elements are made from a polymer. Although the compressible elements 136, 138 may have other compressive stiffness modulii without departing from the scope of the present invention, in one embodiment the elements have a compressive stiffness modulus approximating that of a natural disc. In one embodiment, the compressible elements 136, 138 have uniform and equal undeformed thicknesses of between about 3 mm and about 15 mm. In addition, the implant 130 includes a flexible linkage 140 connecting the upper plate 132 and the lower plate 134 to limit relative motion between the plates. As will be appreciated by those skilled in the art, the configuration of the implant of the second embodiment 130 may provide different intervertebral motions than the configuration of the implant of the first embodiment 100. Therefore, as will be appreciated by those skilled in the art, one configuration may have advantages over another configuration depending upon the specific application. Further, different components may be combined to provide a range of configurations. Because the implant 130 is identical to that of the first embodiment in all other respects, it will not be described in further detail.

Figure 6:
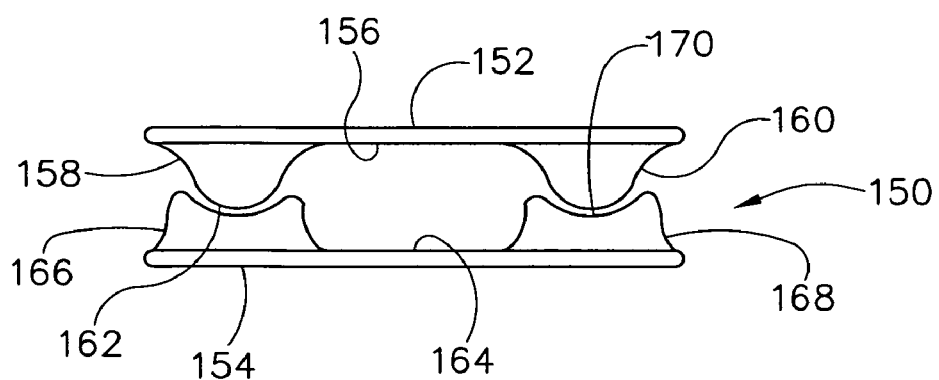
FIG. 6 is a side elevation of an intervertebral implant of a third embodiment.

FIG. 6 illustrates an intervertebral implant of a third embodiment, generally designated by 150. The implant 150 includes an upper plate 152 and a lower plate 154. The upper plate 152 includes a lower face 156 having forward and rearward protrusions 158, 160, respectively, extending downward from the face. These protrusions 158, 160 have convex lower ends 162. The lower plate 154 includes a lower face 164 having forward and rearward protrusions 166, 168, respectively, extending upward from the face. These protrusions 166, 168 have concave upper ends 170 complementing and receiving the convex ends 162 of the upper plate protrusions 158, 160, and allowing the upper and lower plates 152, 154 to pivot with respect to each other. This embodiment does not include compressible elements. Because other features of the implant 150 are identical to those of the first embodiment, they will not be described in further detail.

Figure 7:
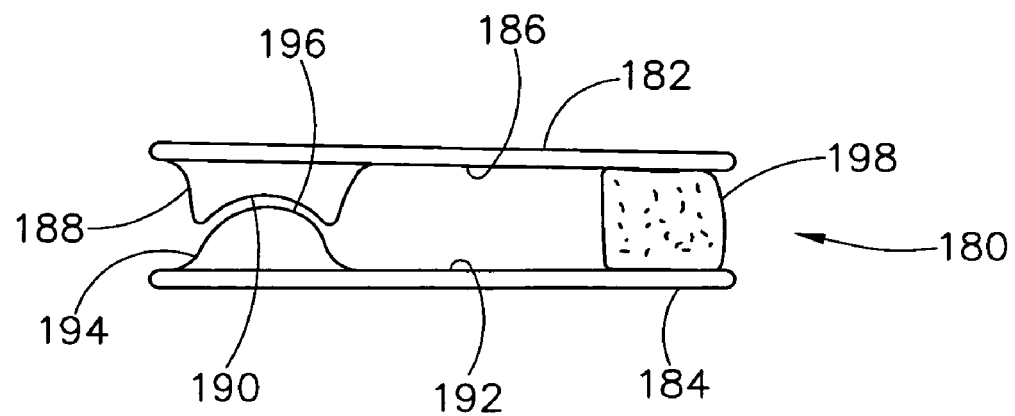
FIG. 7 is a side elevation of an implant of a fourth embodiment.

As shown in FIG. 7, an intervertebral implant of a fourth embodiment is designated in its entirety by the reference number 180. The implant 180 includes an upper plate 182 and a lower plate 184. The upper plate 182 includes a lower face 186 and a protrusion 188 having a concave lower end 190 extending downward from the lower face adjacent one end (e.g., a forward end)). The lower plate 184 includes an upper face 192 and a protrusion 194 having a convex upper end 196 extending upward from the upper face. The concave end 190 of the upper plate protrusion 188 receives the convex end 196 of the lower plate protrusion 194, allowing the plates to pivot. Further, the implant 180 includes a compressible element 198 positioned between the upper and lower plates 182, 184 adjacent an end of the plates opposite the protrusions 188, 194. Because other features of the implant 180 are identical to those of the first embodiment, they will not be described in further detail.

Figure 8:
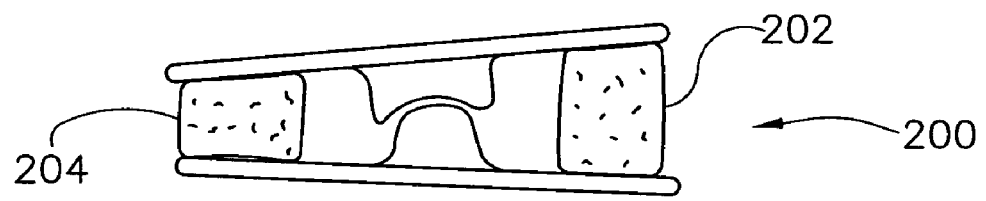
FIG. 8 is a side elevation of an implant of a fifth embodiment.

FIG. 8 shows an implant of a fifth embodiment, generally designated by 200, that is identical to the implant of the first embodiment except that a compressible element 202 on one end has a greater thickness than a compressible element 204 on an opposite end. Although the compressible element 202 may be have other median thicknesses without departing from the scope of the present invention, in one embodiment the element has a median thickness of between about 3 mm and about 17 mm. Although the compressible element 204 may be have other median thicknesses without departing from the scope of the present invention, in one embodiment the element has a median thickness of between about 2 mm and about 10 mm. Further, although the elements 202, 204 may have other included angles without departing from the scope of the present invention, in one embodiment both elements have an included angle of between about 10 degrees and about 35 degrees. In one embodiment, the element 204 having the greater thickness is the forward element.

Figure 9:
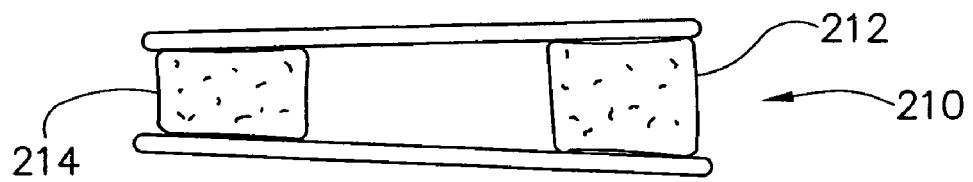
FIG. 9 is a side elevation of an implant of a sixth embodiment.

FIG. 9 shows an implant of a sixth embodiment, generally designated by 210, that is identical to the implant of the second embodiment except that a compressible element 212 on one end has a greater thickness than a compressible element 214 on an opposite end. Although the compressible element 212 may be have other median thicknesses without departing from the scope of the present invention, in one embodiment the element has a median thickness of between about 3 mm and about 17 mm. Although the compressible element 214 may be have other median thicknesses without departing from the scope of the present invention, in one embodiment the element has a median thickness of between about 2 mm and about 12 mm. Further, although the elements 212, 214 may have other included angles without departing from the scope of the present invention, in one embodiment both elements have an included angle between about 10 degrees and about 35 degrees. In one embodiment, the element 214 having the greater thickness is the forward element.

Figure 10:
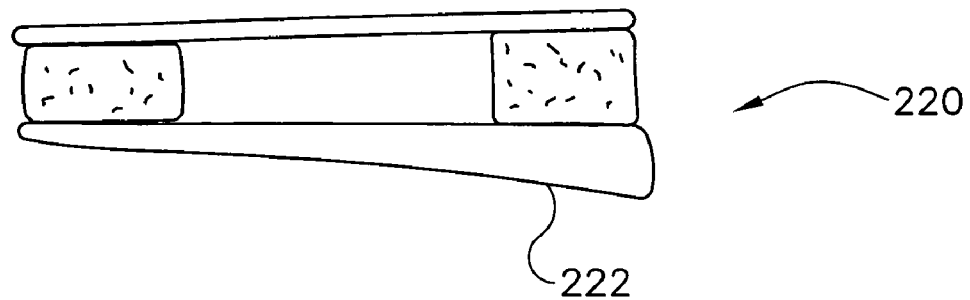
FIG. 10 is a side elevation of an implant of a seventh embodiment.

FIG. 10 illustrates an implant of a seventh embodiment, generally designated by 220, that is identical to the implant of the second embodiment except that the seventh embodiment has a lower plate 222 having a varying thickness. Although exterior surfaces of the plate 222 may have other included angles without departing from the scope of the present invention, in one embodiment the plate surfaces have an included angle between about 10 degrees and about 35 degrees. In one embodiment, the plate 222 has a greater thickness at its forward end.

Figure 11:
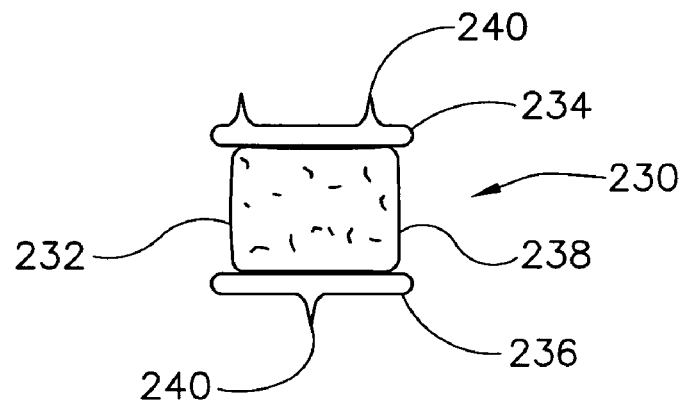
FIG. 11 is a rear elevation of an implant of an eighth embodiment.

As shown in FIG. 11, an implant of an eighth embodiment is generally designated 230. This embodiment is similar to the implant of the second embodiment except it only has one compressible element 232 positioned between an upper plate 234 and a lower plate 236. The element extends between a forward end and a rearward end (not shown) of the implant 230 and between opposite lateral sides 238 of the implant. In addition, the upper and lower plates 234, 236, respectively, include longitudinal anchors 240 for anchoring each of the plates to its respective vertebra. In one embodiment, the upper plate 234 includes two spaced anchors 240 and the lower plate 236 includes one central anchor 240.

Figure 12:
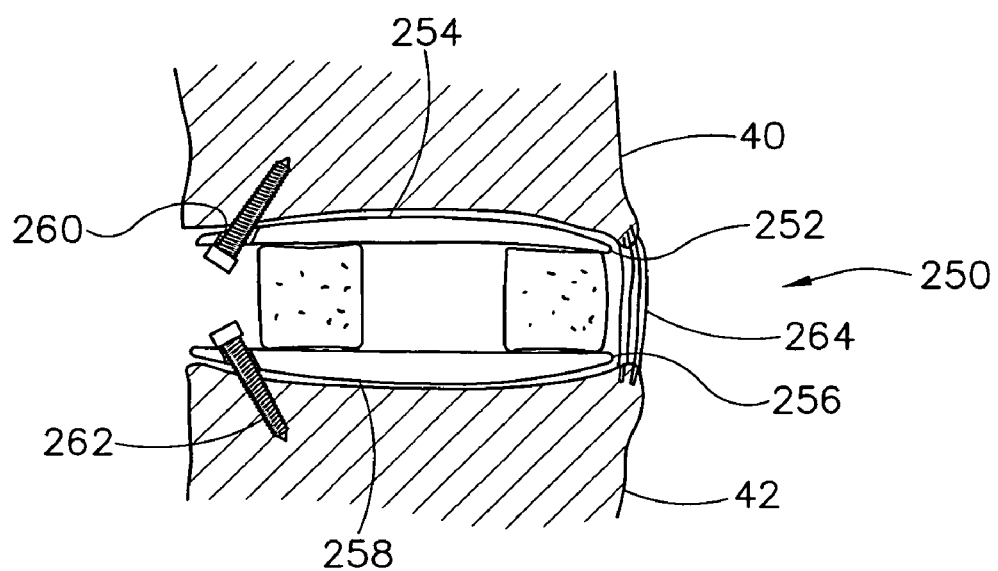
FIG. 12 is a cross section of an implant of a ninth embodiment.

FIG. 12 illustrates a ninth embodiment of an implant generally designated 250. The ninth embodiment is similar to the second embodiment except it has an upper plate 252 including a rounded upper surface 254 and a lower plate 256 has a rounded lower surface 258 to increase a contact area with the corresponding vertebrae. The upper and lower plates 252, 256, respectively, each include an opening 260 sized and positioned for receiving a screw fastener 262 for anchoring the plates to the respective vertebrae 40, 42. In one embodiment, each of the plates 252, 256 include one opening 260. In other embodiments, the plates 252, 256 may include more openings without departing from the scope of the present invention. As will be apparent to those skilled in the art, the implant 250 of the ninth embodiment may in installed without removing the strong ligament 264 extending between the vertebrae 40, 42.

Figure 13:
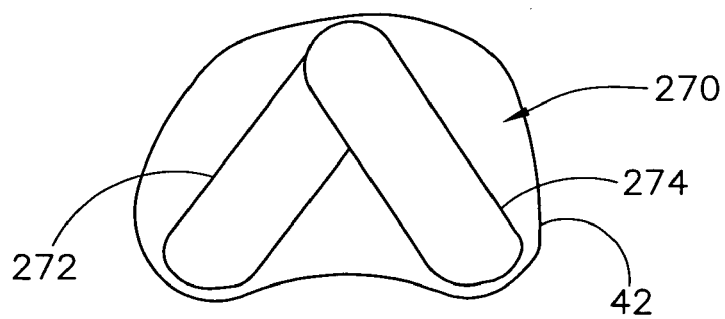
FIG. 13 is a top plan of an implant of a tenth embodiment.
Figure 14:
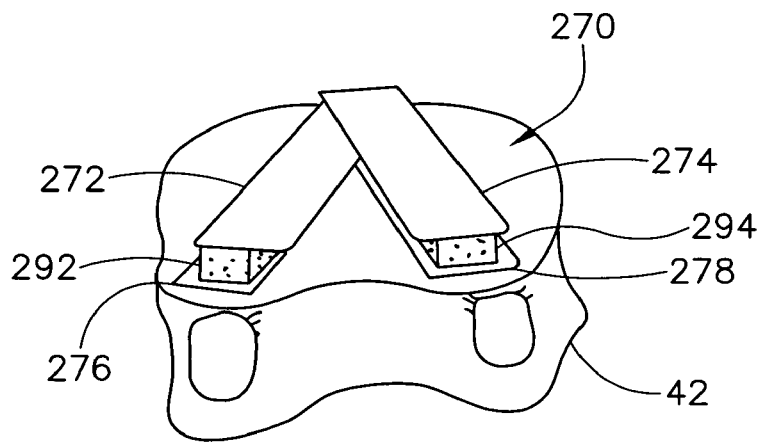
FIG. 14 is a perspective of the implant of FIG. 13.
Figure 15:
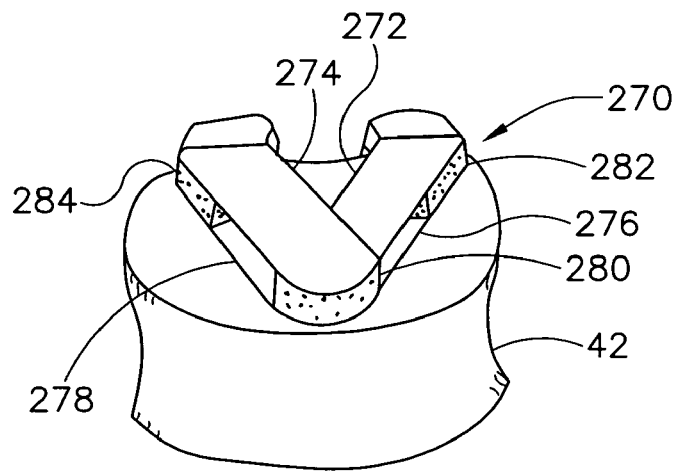
FIG. 15 is a second perspective of the implant of FIG. 13.

FIGS. 13-15 illustrate an implant of a tenth embodiment, generally designated by 270. The implant 270 includes two upper plates 272, 274 overlapped at one end and arranged in a V-shape as shown. The implant 270 also includes two lower plates 276, 278 overlapped at one end and also arranged in a V-shape as shown. Although the upper and lower plates 272, 274, 276, 278 may be overlapped at other ends without departing from the scope of the present invention, in one embodiment, the plates are overlapped at their forward ends. A forward compressible element 280 is positioned between the upper and lower plates 272, 280. Rearward compressible elements 282, 284 are positioned between respective rearward ends of the upper and lower plates as shown. The plates may be fastened together using conventional means such as interlocking parts, riveting or brazing. Although the upper plates 272, 274 and lower plates 276, 278 may be arranged to form other included angles, in one embodiment, both the upper and lower plates define included angles of between about 15 degrees and about 90 degrees.

Figure 16:
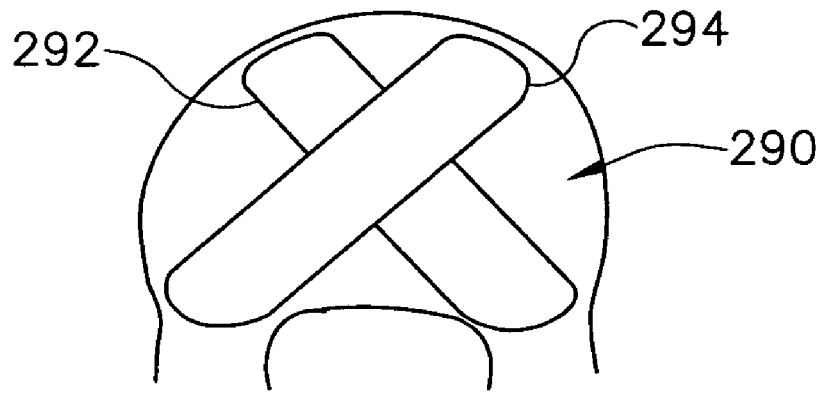
FIG. 16 is a top plan of an intervertebral implant of an eleventh embodiment of the present invention.
Figure 17:
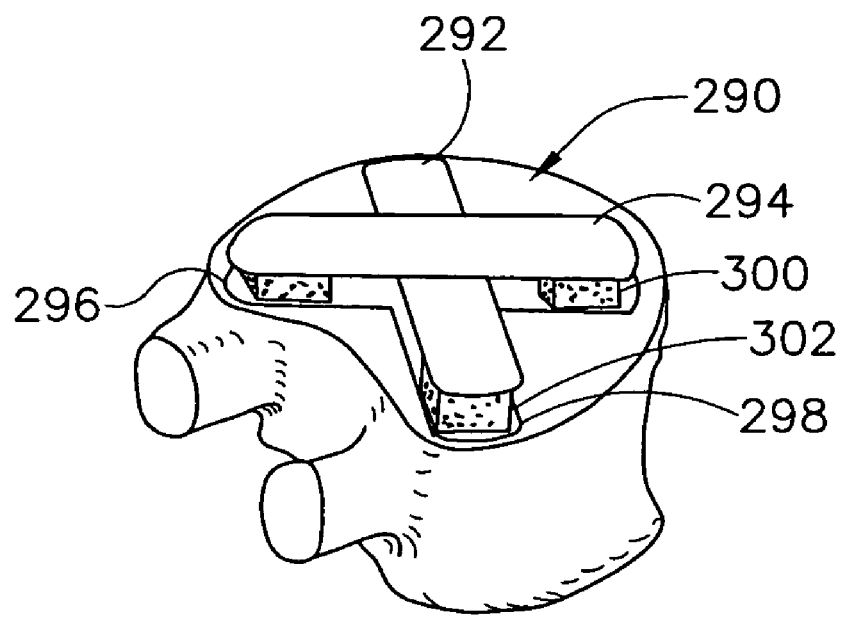
FIG. 17 is a perspective of the implant of FIG. 16.
Figure 18:
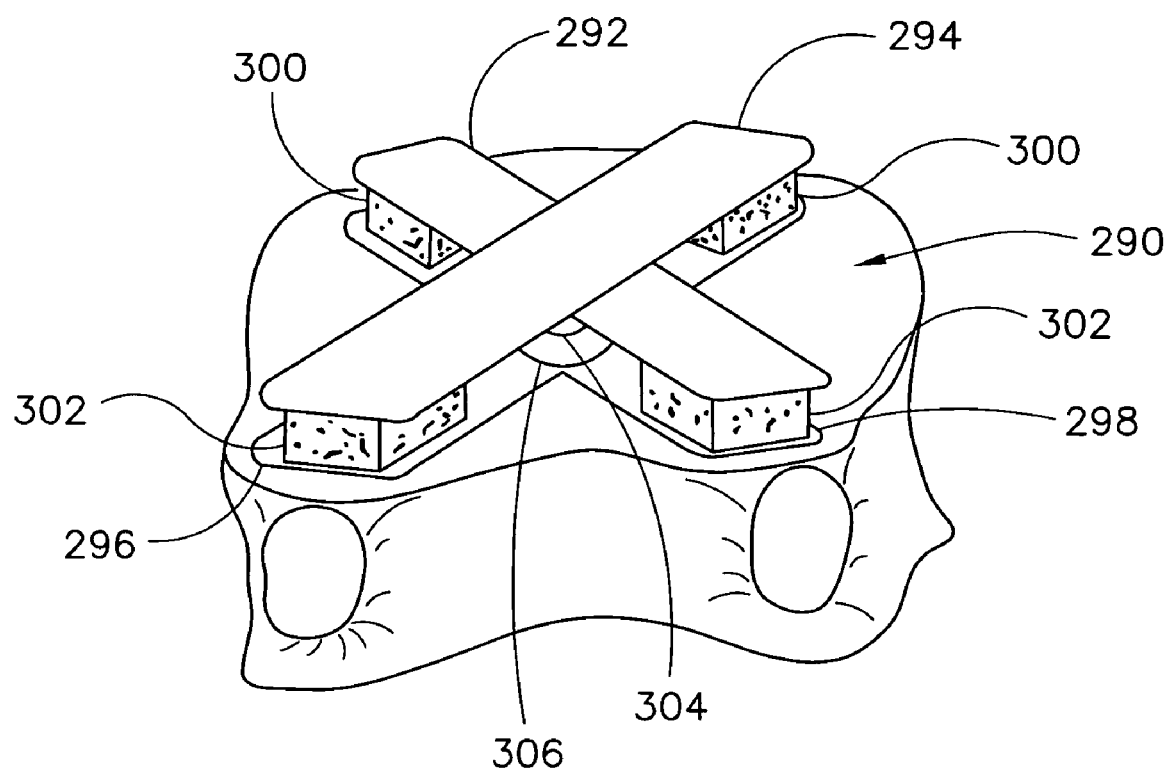
FIG. 18 is a second perspective of the implant of FIG. 16.

FIGS. 16-18 illustrate an implant of an eleventh embodiment, generally designated by 290 including two upper plates 292, 294 and two lower plates 296, 298. The upper plates 292, 294 are overlapped between their ends and arranged in an X-shape, and the lower plates 296, 298 are overlapped between their ends and arranged in an X-shape as shown. Forward compressible elements 300 are positioned between forward ends of the upper and lower plates 292, 294, 296, 298, and rearward compressible elements 302 are positioned between rearward ends of the upper and lower plates. In one embodiment, the inner upper and lower plates 292, 298 have interengaging protrusions 304, 306 similar to the plates of the first embodiment. Because the implant 290 of the eleventh embodiment is similar to the implant 270 of the tenth embodiment in all other respects, the implant of the eleventh embodiment will not be described in further detail.

As will be appreciated by those skilled in the art, the tenth and eleventh embodiments may be assembled outside the patient and surgically implanted using conventional techniques. In another embodiment, at least a portion of a natural disc is removed from between an upper vertebra and a lower vertebra using conventional techniques. A first component of the implant (e.g., upper plate 272) is inserted between the upper vertebra and the lower vertebra. Then, a second component of the implant (e.g., upper plate 274) is inserted between the upper vertebra and the lower vertebra. Once both components are in place, they are connected together. As will be apparent to those skilled in the art, the first and second components may be inserted along different lines of entry, and those lines of entry may be obliquely oriented with respect to each other. In addition, other aspects and features of this method use conventional surgical techniques and will be understood by those skilled in the art from this description.

Figure 19:
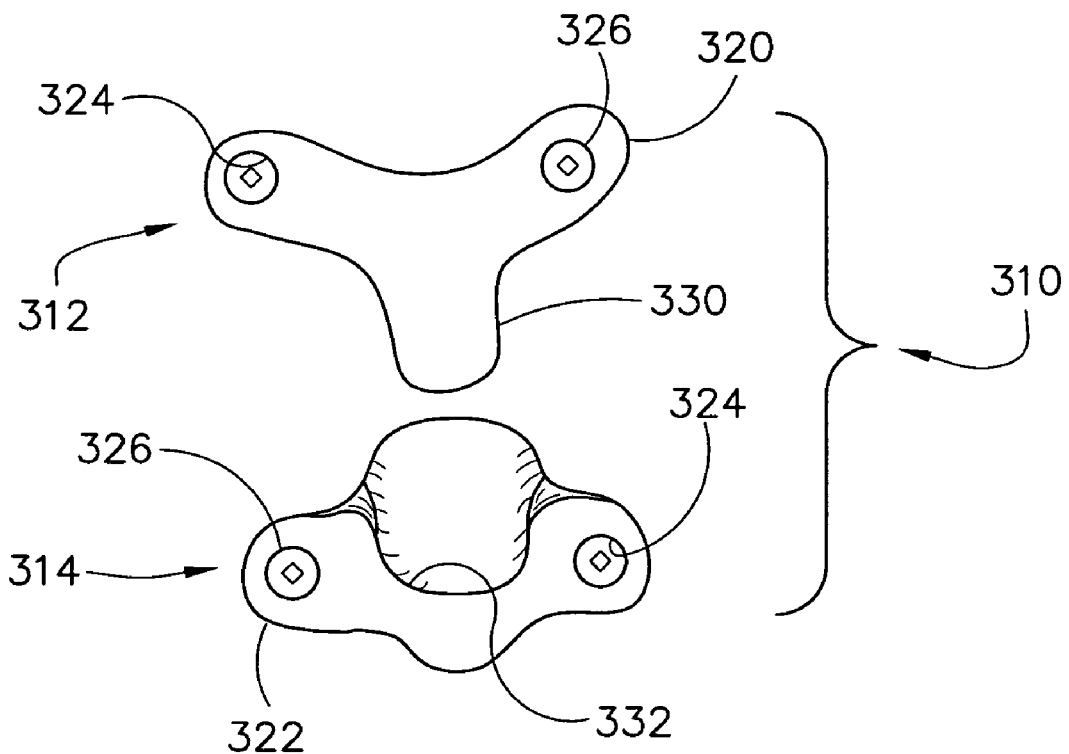
FIG. 19 is a separated rear elevation of an implant of a twelfth embodiment.
Figure 20:
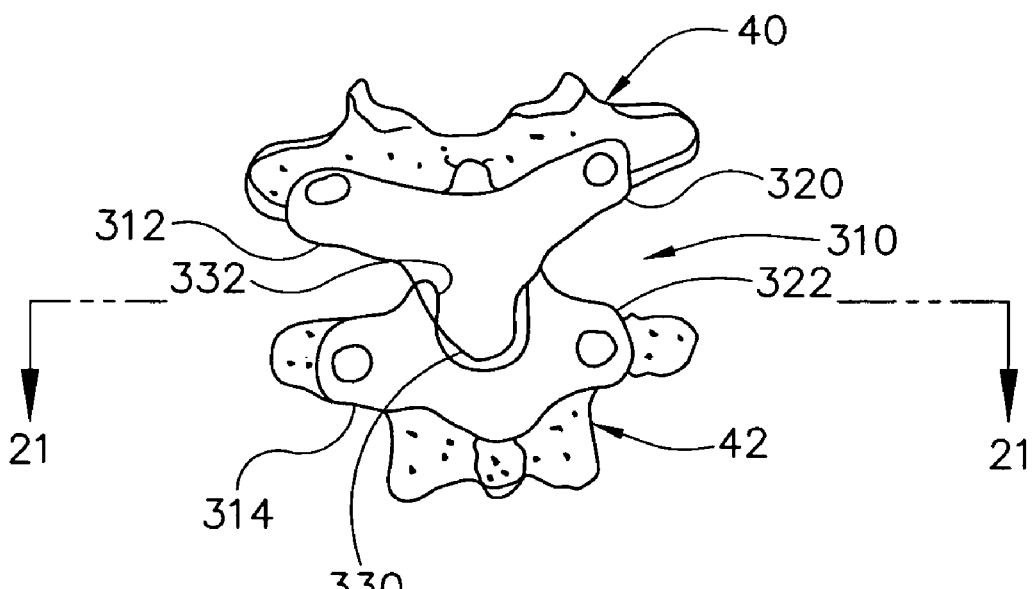
FIG. 20 is an assembled rear elevation of the implant of FIG. 19.
Figure 21:
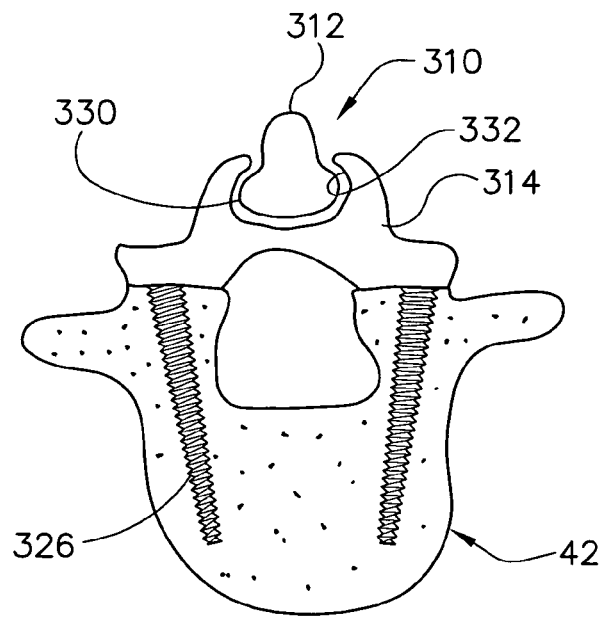
FIG. 21 is cross section the implant of the twelfth embodiment taken along line 21-21 of FIG. 20.

FIGS. 19-21 illustrate an implant of a twelfth embodiment generally designated by 310. This implant 310 includes an upper portion (generally designated by 312) and a lower portion (generally designated by 314). The upper portion 312 includes two lobes 320, and the lower portion 314 includes two lobes 322. Each of the lobes 320, 322 has an opening 324 sized for receiving bone attachment elements such as conventional pedicle screws 326. The openings 324 are positioned so the screws 326 may be anchored to the pedicles 46 of the vertebrae 40, 42. The upper portion 312 includes a post or protrusion 330 extending downward from and centrally located between the lobes 320. The lower portion 314 includes a central channel 332 defined by two ribs 334. The channel 332 is sized and shaped for receiving the post 330 of the corresponding upper portion 312 so the post moves freely in the channel, allowing substantial motion between the vertebrae 40, 42. The upper and lower portions 312, 314 may be made from any suitable material such as a cobalt alloy, surgical steel, carbon composite, ceramic or polymer and may be made in a variety of sizes to fit different size people. As illustrated in FIG. 21, portions of the vertebrae 40, 42 (e.g., portions of the spinous processes 52 and the lamina 48) may be removed to provide a planar surface upon which to mount the upper and lower portions, 312, 314 of the implant.

Figure 22:
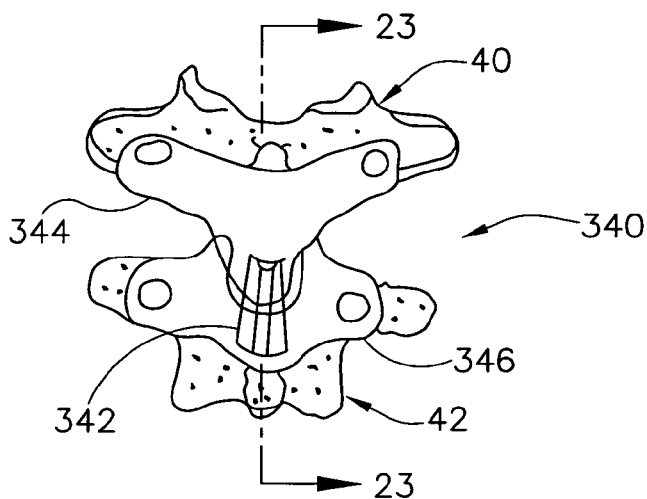
FIG. 22 is a rear elevation of an implant of a thirteenth embodiment.
Figure 23:
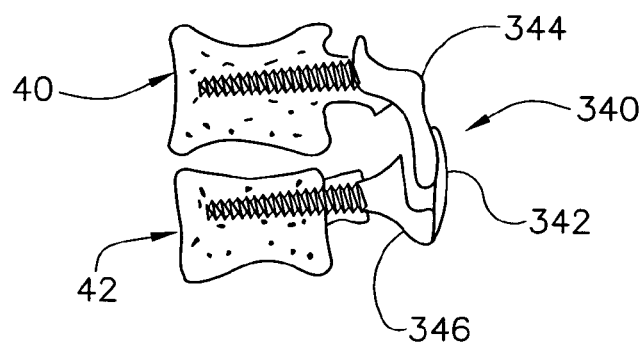
FIG. 23 is a cross section of the implant of the thirteenth embodiment taken along line 23-23 of FIG. 22.

FIGS. 22 and 23 show a thirteenth embodiment of an implant, generally designated by 340. This implant 340 is substantially identical to the twelfth embodiment except it includes a linkage or synthetic ligament 342 connecting its upper and lower portions 344, 346, respectively. The linkage 342 allows the upper and lower portions 344, 346 to articulate, rotate, extend and contract, but prevents the portions from becoming disengaged. Although the linkage 342 may be made of other materials without departing from the scope of the present invention, in one embodiment the linkage is made of polyester.

Figure 24:
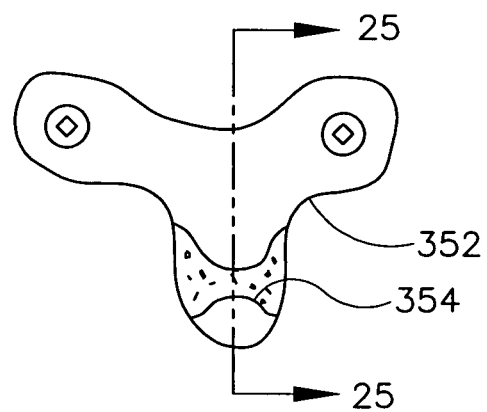
FIG. 24 is a rear elevation of an upper portion of an implant of a fourteenth embodiment.
Figure 25:
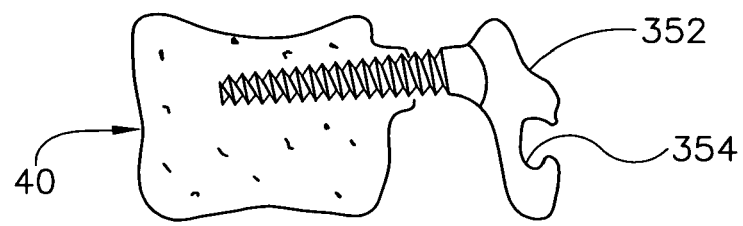
FIG. 25 is a cross section of the upper portion of the implant of the fourteenth embodiment taken along line 25-25 of FIG. 24.
Figure 26:
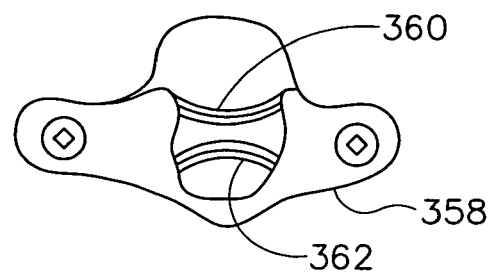
FIG. 26 is a rear elevation of a lower portion of the implant of the fourteenth embodiment.
Figure 27:
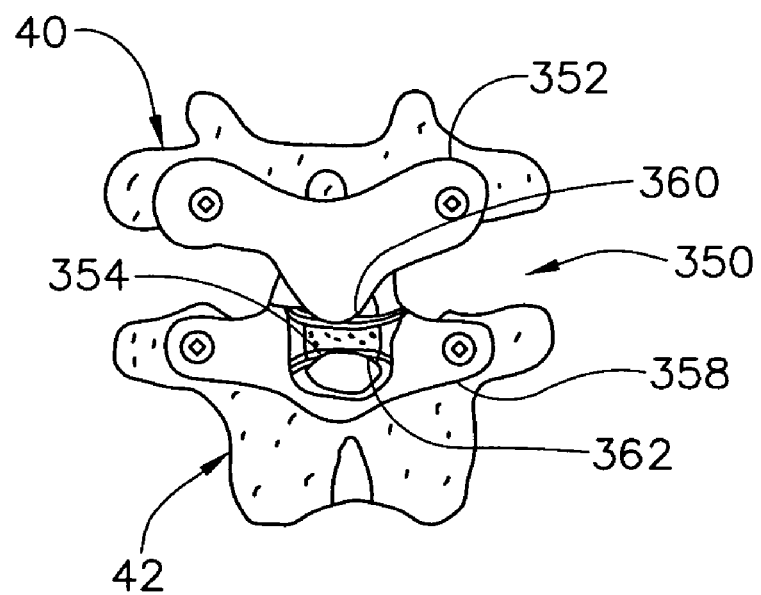
FIG. 27 is an assembled rear elevation of the implant of the fourteenth embodiment.

FIGS. 24-27 show an implant 350 of a fourteenth embodiment of the present invention. As illustrated in FIGS. 24 and 25, an upper portion 352 of the fourteenth embodiment of the implant 350 is substantially identical to the upper portion 312 of the twelfth embodiment except it includes a bowtie-shaped opening 354 extending laterally across the post 356. As shown in FIG. 26, a lower portion 358 of the fourteenth embodiment of the implant 350 is substantially identical to the lower portion 314 of the twelfth embodiment except it includes elastic or ligamentous elements 360, 362 extending across the channel 364. Although the elastic or ligamentous elements 360, 362 may be made of other materials without departing from the scope of the present invention, in one embodiment the elements are made of polyester. When assembled as shown in FIG. 27, the post 356 of the upper portion 352 of the implant 350 is inserted in the channel 364 until the elastic elements 360, 362 are positioned in the opening 354 in the post to prevent the upper and lower portions from becoming disengaged and limiting excessive motion. Because the implant 350 is identical to the implant 310 of the twelfth embodiment in all other respects, it will not be described in further detail.

Figure 28:
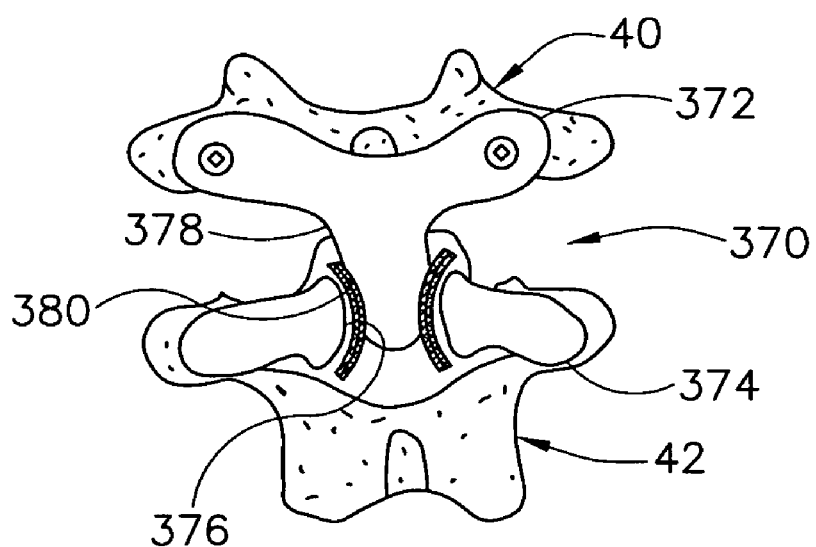
FIG. 28 is a rear elevation of an implant of a fifteenth embodiment.

FIG. 28 shows an implant 370 of a fifteenth embodiment of the present invention. This implant 370 is substantially identical to the twelfth embodiment, having an upper portion 372 and a lower portion 374. The lower portion 374 has a channel 376 having convex rounded sides shaped to receive a post 378 of the upper portion 372 and to allow the upper portion to pivot or tilt from side to side relative to the lower portion. Flexible or deformable components 380 are mounted on both sides of the post 378 to permit compliance and provide cushioning as the upper and lower portions move relative to each other. Although the components 380 may be made of other materials without departing from the scope of the present invention, in one embodiment the components are made of stainless steel.

Figure 29A:
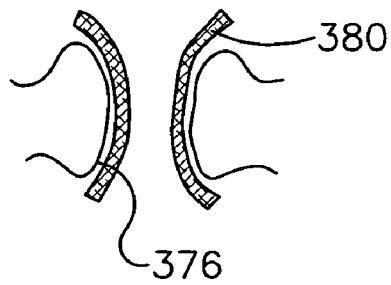
FIGS. 29a-29c are schematics of the implant of FIG. 28 showing relative movement between portions.
Figure 29B:
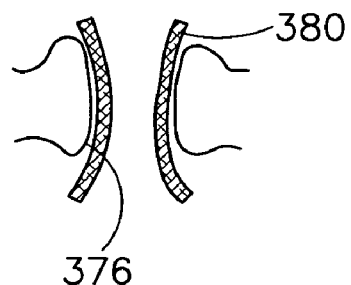
Figure 29C:
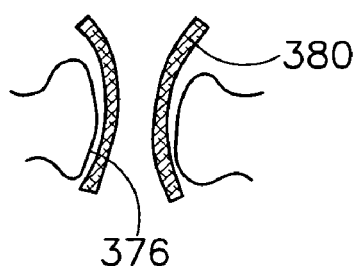

FIG. 29a illustrates the upper and lower portions 372, 374 of the implant 370 in a neutral unloaded position. The flexible components 380 move with the upper portion 292 between a raised position shown in FIG. 29b and a lowered position shown in FIG. 29c. The components 380 stretch and straighten as the upper and lower portions 372, 374 move away from the neutral position thereby increasing forces acting on the portions to move the portions back toward their neutral position. Thus, the components 380 bias the portions 372, 374 toward their neutral positions and limit relative movement.

Figure 30:
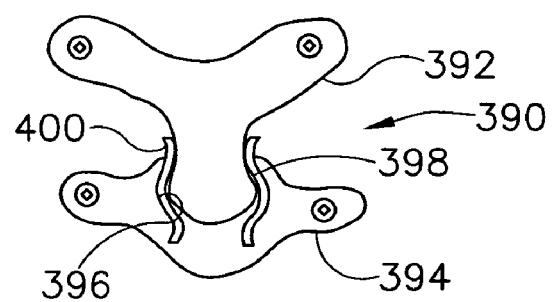
FIG. 30 is a rear elevation of an implant of a sixteenth embodiment.

FIG. 30 illustrates an implant 390 of a sixteenth embodiment of the present invention. This implant 390 is substantially identical to the twelfth embodiment, having an upper portion 392 and a lower portion 394. The lower portion 394 has a channel 396 including concave rounded sides shaped to receive a post 398 of the upper portion 392 having convex sides and to allow the upper portion to pivot from side to side relative to the lower portion. Flexible or deformable components 400 are mounted on both sides of the channel 396 to permit compliance and provide cushioning as the upper and lower portions move relative to each other. Although the components 400 may be made of other materials without departing from the scope of the present invention, in one embodiment the components are made of stainless steel.

Figure 31A:
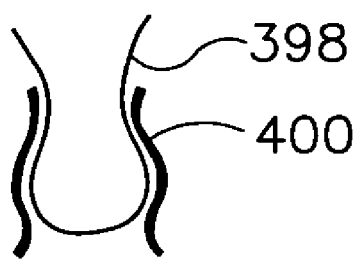
FIGS. 31a and 31b are schematics of the implant of FIG. 30 showing relative movement between portions.
Figure 31B:
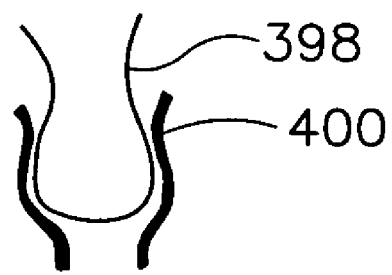

FIG. 31a shows the upper and lower portions 392, 394 of the implant 390 in a neutral unloaded position. The flexible or deformable components 400 move with the lower portion 394 between a raised position shown in FIG. 31b and a lowered position (not shown). The components 400 deform as the upper and lower portions 392, 394 move away from the neutral position thereby increasing forces acting on the portions to move the portions back toward their neutral position. Thus, the components 400 bias the portions 392, 394 toward their neutral positions and limit relative movement.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An intervertebral implant for spacing an upper vertebra and a lower vertebra comprising:
   an upper mount including a plurality of plates arranged in an X-shape, each of said plates having an upper surface sized and shaped for engaging the upper vertebra and a lower surface opposite the upper surface, the upper surfaces of the plates facing in generally the same upward direction and each of said upper surfaces being positioned for directly engaging the upper vertebra;
   a lower mount including a plurality of plates arranged in an X-shape, each of said plates having a lower surface sized and shaped for engaging the lower vertebra and an upper surface opposite the lower surface, the lower surfaces of the plates facing in generally the same downward direction and each of said lower surfaces being positioned for directly engaging the lower vertebra; and
   an element positioned between the upper mount and the lower mount spacing the upper surface of the upper mount from the lower surface of the lower mount by a predetermined distance, said element being configured to permit the upper mount to pivot downward relative to the lower mount, thereby allowing the upper vertebra to pivot downward relative to the lower vertebra while maintaining spacing between the upper vertebra and the lower vertebra.

2. An implant as set forth in claim 1 wherein the element comprises a first portion having a convex surface, and a second portion having a concave surface positioned for engaging the convex surface.

3. An implant as set forth in claim 2 wherein the element further comprises an elastomeric element positioned between the lower surface of the upper mount and the upper surface of the lower mount for permitting and at the same time resisting pivotal movement between the upper mount and the lower mount.

4. An implant as set forth in claim 2 wherein the element further comprises a plurality of elastomeric elements positioned between the upper mount and the lower mount for permitting and at the same time resisting pivotal movement between the upper mount and the lower mount, at least one of said plurality of elastomeric elements being positioned in front of the convex and concave surfaces, and at least one of said plurality of elastomeric elements being positioned behind the convex and concave surfaces.

5. An implant as set forth in claim 1 wherein:
   the element includes a projection extending downward from a lower surface of the upper mount and a projection extending upward from an upper surface of the lower mount; and
   one of said projections includes a convex surface, and another of said projections includes a concave surface positioned for engaging the convex surface.

6. An implant as set forth in claim 5 wherein:
   the projection extending downward from the upper mount includes the concave surface; and
   the projection extending upward from the lower mount includes the convex surface.

7. An implant as set forth in claim 1 wherein the plates of the upper mount each have a longitudinal axis and are positioned with respect to each other so the longitudinal axes of the plates of the upper mount are nonparallel, and the plates of the lower mount each have a longitudinal axis and are positioned with respect to each other so the longitudinal axes of the plates of the lower mount are nonparallel.

8. An implant as set forth in claim 1 wherein the plates of the upper mount overlap each other and the plates of the lower mount overlap each other.

* * * * *